United States Patent [19]

Brennensholtz et al.

[11] Patent Number: 4,552,459
[45] Date of Patent: Nov. 12, 1985

[54] SURFACE REFLECTIVITY DEVICE AND METHOD

[75] Inventors: Matthew S. Brennensholtz, Waterloo; Robert L. Donofrio, Elbridge, both of N.Y.

[73] Assignee: North American Philips Consumer Electronics Corp., New York, N.Y.

[21] Appl. No.: 423,902

[22] Filed: Sep. 27, 1982

[51] Int. Cl.[4] ......................................... G01N 21/48
[52] U.S. Cl. .................................................. 356/448
[58] Field of Search ............... 356/445, 446, 447, 448, 356/244; 250/571

[56] References Cited

U.S. PATENT DOCUMENTS

| 2,954,266 | 9/1960 | Danielson et al. | 356/398 |
| 3,817,628 | 6/1974 | Adams | 356/448 |
| 4,029,420 | 6/1977 | Simms | 356/448 |
| 4,030,837 | 6/1977 | Kojima et al. | 356/445 |
| 4,050,820 | 9/1977 | Hanny | 356/446 |
| 4,054,391 | 10/1977 | Witte | 356/445 |
| 4,260,262 | 4/1981 | Webster | 356/448 |
| 4,406,545 | 9/1983 | Montone et al. | 356/445 |
| 4,444,499 | 4/1984 | Akiyama et al. | 356/448 |

Primary Examiner—R. A. Rosenberger
Attorney, Agent, or Firm—John C. Fox

[57] ABSTRACT

A device and method for measuring the reflectivity of the tungsten oxide surface coating on cathode ray tube heaters are described, in which selected small areas of an illuminated heater wire turns are scanned by a microscope, and the collected reflected light converted to voltage values by a photomultiplier tube and compared to a standard value.

2 Claims, 2 Drawing Figures

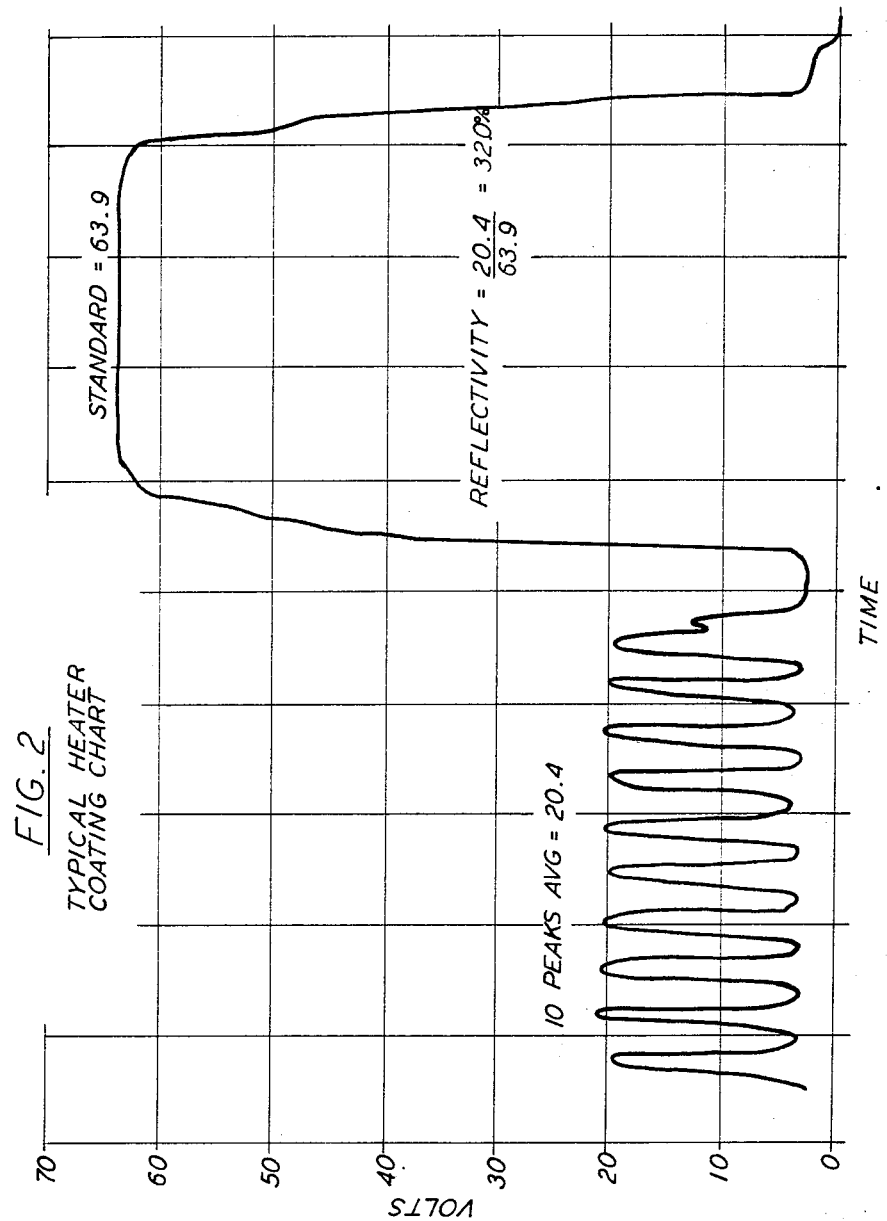

SURFACE REFLECTIVITY DEVICE AND METHOD

BACKGROUND OF THE INVENTION

1. Field Of The Invention

This invention relates to a device and method for measuring reflectivity of small irregular surfaces, and more particularly relates to measuring reflectivity of the surface coating on cathode ray tube heaters.

2. Prior Art

When current is applied to the heater in a cathode ray tube, heat is produced due to the resistance of the heater wire. The heat flows to the cathode and to the emissive material on the cathode causing electrons to emit and flow through the gun to the screen of the cathode ray tube. The amount of electrons emitted from the emissive material is a function of the amount of heat applied to it, so it is important to control heater characteristics.

The shade (also called reflectivity or emissivity) of the heater coating for cathode ray tubes is an important characteristic because heat is removed from the heater by radiation. Shade is controlled by a multicoating process. The undercoat is aluminum oxide which results in a white color coating. The overcoat is a darker coating of tiny tungsten particles. The more dark particles that cover the white coating, the darker the shade. Cathode temperature is a function of the amount of power supplied to the heater. Power is controlled by voltage and current. Since heater voltage is normally fixed at either 6.3 or 7.1 volts, any variation in heater power is due to variation in heater current. Heater current is controlled by three main factors; heater design, wire thickness and heater shade. Heater shade affects the current because the wire used in the heater is normally tungsten or a tungsten alloy and the resistance of the wire varies with temperature. Thus, with a darker shade of overcoat, energy is radiated away from the heater faster, the heater runs cooler, the resistance of the wire decreases, the current increases and the power of the heater increases. Thickness of the wire has a similar effect. When wire thickness increases, the resistance decreases, the current increases and the power increases.

Wire thickness varies from lot to lot, and it is difficult to obtain wire having thicknesses controlled within limits sufficient to maintain the heater power within acceptable limits. Thus, it is necessary to change the shade of heaters to compensate for the variation in heater wire thickness.

Means that are presently available to measure reflectivity of this coating include visual inspection using photo gray shade cards and an optical reflectance device, both of which are acceptable for measuring reflectivity of large areas but are unsatisfactory to measure reflectivity of cathode heaters because the heaters have small irregular surfaces. Use of either device results in poor repeatability of readings, poor accuracy and calibration difficulties. Also, the optical reflectance method prevents comparison of the reflectivity of different heater types because the readings include the background and all the coils. Thus, readings will vary as the size of the wire or the number or size of the coils vary with different heater types.

Accordingly, objectives of the present invention include: providing a device which will improve repeatability of readings, improve accuracy, reduce calibration difficulties and permit comparison of reflectivity measurements for different heater types.

SUMMARY OF THE INVENTION

A method for measuring reflectivity of small irregular surfaces is described, the method comprising: illuminating at least a portion of the surface; collecting the reflected light from selected areas of such illuminated portion; sensing the intensity of such reflected light and converting it to electrical signals proportional to the intensity of the reflected light; and comparing the average peak values of such reflected intensity with a standard value to obtain a ratio.

In a preferred emodiment, the reflected light is collected by scanning the surface, for example, of the configurated portion of cathode ray tube heaters, with a microscope focused on the selected areas to be measured. Microscope field of view is typically 30 to 50% of the heater wire diameter.

A device for carrying out the method is also described, the device comprising: sample holding means having a light absorbing surface at least in the area under the sample; a light reflective surface as a standard; means for illuminating the sample in its holder and the standard, means for collecting reflected light from selected small areas of the sample surface and from the standard; and means to sense the intensities of the reflected light and to convert such intensities into electrical signals proportional to the amount of light reflected.

BRIEF DESCRIPTION OF THE DRAWINGS

FIG. 2 is a chart of voltage versus time showing the voltages produced by reflectivity measurements of a black background, a "white" standard and a typical heater coil.

DESCRIPTION OF THE PREFERRED EMBODIMENT

Figure 1:
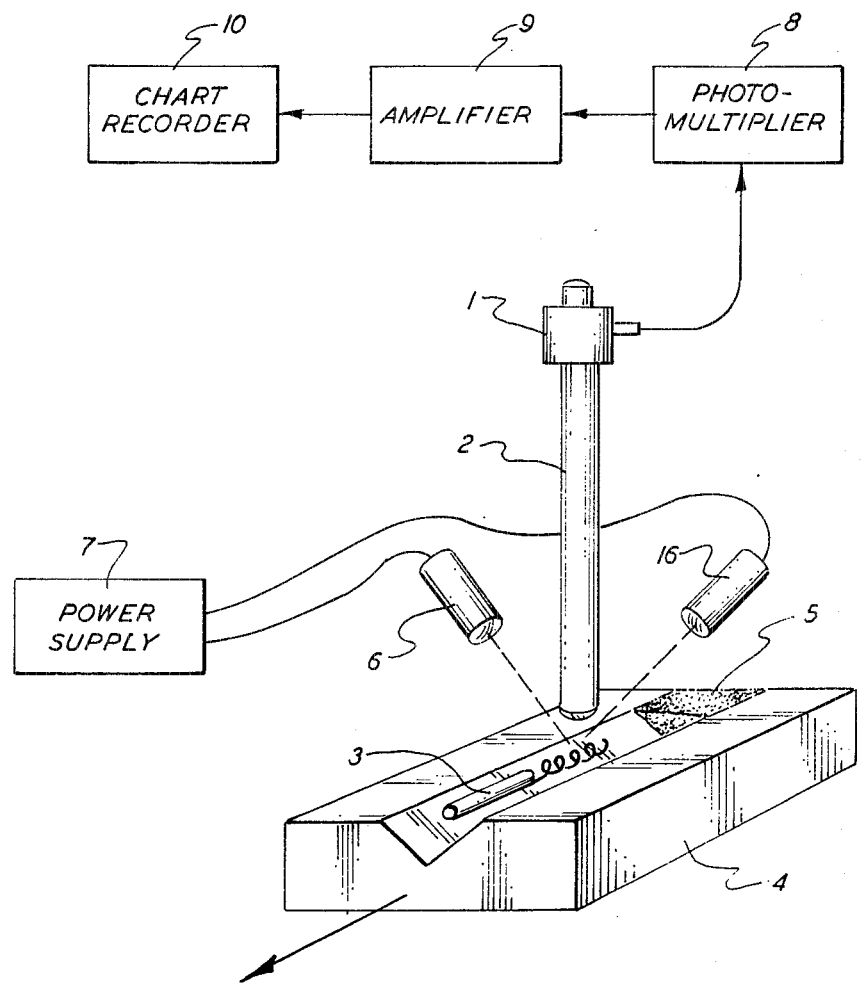
FIG. 1 is a perspective view and block diagram showing one embodiment of the invention.

Referring now to FIG. 1, there is shown one embodiment of the reflectivity measuring device of the invention, wherein a fiber optic eye piece 1 with an apparent diameter of 4.5 mils is mounted to a 60× microscope 2. This arrangement allows focusing selectively on small areas of the heater coating. The heater 3 is located in the "V" of a movably mounted block 4 to ensure against lateral movement and is scanned parallel to the axis of the "V" as the block 4 moves along this axis. The heater coating reflectivity is compared to that of a $BaSO_4$ flat white standard coating 5 which is assumed to have approximately 100% reflectance. The height of the white standard 5 is adjusted to the same level as the top of the heater 3. The lamps 6, standard low voltage incandescent lamps powered by a regulated power supply 7, are positioned to illuminate the black background of the "V", the white standard and heater whose coating reflectivity is to be measured. The background for the heater is black, by a black coating on the "V".

The reflected light intensities are converted to voltage values by a photo-multiplier tube, 8, amplified by amplifier 9 and plotted on a chart recorder 10. Preferably the white standard 5 is sampled a number of times to establish an average voltage value for 100% reflectivity. Next, a heater sample is measured. FIG. 2 is a sample chart for such measurements. The signal produced by the black background produces a nearly zero voltage. To determine a reflectivity value, the peaks are averaged and divided by the average value of the standard. Each peak represents one turn of the heater coil. The heater measured by the chart of FIG. 2 had ten turns, but some heater types have as many as twenty or more turns.

Both the top and bottom of a heater are preferably measured, then averaged, since at times such measurements differ by as much as ten percent (10%).

While the invention has been described in terms of an exemplary embodiment, other embodiments will occur to those skilled in the art. For example, the photomultiplier and fiber optic means may both be replaced by a silicon photocell placed directly in the microscope eyepiece. In addition, the chart recorder may be replaced or augmented by a microprocessor unit which could automatically compute the desired relative reflectance values.

We claim:

1. A method for measuring surface reflectivity of a coiled wire sample having a plurality of turns, the method comprising:

placing the sample under a microscope having a field of view smaller than the wire diameter;

illumnating the sample;

focusing the microscope upon a portion of the surface of a single turn of the sample;

scanning the sample with the microscope to cause the field of view of the microscope to move successively from the surface of one turn to another, to successively collect the reflected light from such scanned surfaces;

continuously sensing the intensity of the successively collected reflected light and converting it to electrical signals proportional to the varying intensity of the reflected light; and comparing the average peak values of such varying reflected intensity with a standard value to obtain a ratio.

2. The method of claim 1 in which the field of view of the microscope is from about 30 to 50 percent of the wire diameter.

* * * * *